United States Patent [19]

Nagase et al.

[11] 3,931,280
[45] Jan. 6, 1976

[54] PROCESS FOR PREPARING ALKYL TRANS-CHRYSANTHEMATE

[75] Inventors: Tsuneyuki Nagase, Takatsuki; Gohu Suzukamo, Ibaraki; Masami Fukao, Takatsuki; Hirosuke Yoshioka, Ikeda, all of Japan

[73] Assignee: Sumitomo Chemical Company, Limited, Japan

[22] Filed: Sept. 7, 1973

[21] Appl. No.: 395,150

[30] Foreign Application Priority Data
Sept. 7, 1972 Japan.............................. 47-90223

[52] U.S. Cl. ............................................. 260/468 H
[51] Int. Cl.² ......................................... C07C 67/30
[58] Field of Search .................... 260/514 H, 468 H

[56] References Cited
UNITED STATES PATENTS

| | | | |
|---|---|---|---|
| 3,046,299 | 7/1962 | Julia.................................... | 260/468 |
| 3,538,143 | 11/1970 | Matsui et al. ...................... | 260/468 |

*Primary Examiner*—Robert Gerstl
*Attorney, Agent, or Firm*—Stewart and Kolasch, Ltd.

[57] ABSTRACT

Alkyl cis-chrysanthemate is treated with a catalytic amount of alkali metal alkoxide at a temperature of about 50° to 200°C in the absence or presence of an aprotic solvent to give alkyl trans-chrysanthemate in a high purity and an excellent yield.

6 Claims, No Drawings

PROCESS FOR PREPARING ALKYL TRANS-CHRYSANTHEMATE

The present invention relates to a process for preparing alkyl trans-chrysanthemate, i.e. alkyl 2,2-dimethyl-3-(2'-methyl)-1'-propenyl-1,3-trans-cyclopropane-1-carboxylate. More particularly, it relates to a process for preparing the said trans-isomer from the corresponding cis-isomer, i.e. alkyl 2,2-dimethyl-3-(2'-methyl)-1'-propenyl-1,3-cis-cyclopropane-1-carboxylate, by the use of a catalytic amount of alkali metal alkoxide.

It is known that chrysanthemic acid is the acid component of the esters known as "pyrethroidal insecticides" such as pyrethrin, allethrin, phthalthrin and 5-benzyl-3-furylmethyl chrysanthemate. It is also known that the pyrethroids having the residue of trans-chrysanthemic acid as the acid component generally exhibit a higher insecticidal activity than those having the residue of cis-chrysanthemic acid as the acid component. Thus, the use of the transisomer of chrysanthemic acid for the production of pyrethroids is more advantageous and favorable than that of the corresponding cis-isomer.

For the production of alkyl chrysanthemate, there has heretofore been widely adopted the reaction of 2,5-dimethyl-2,4-hexadiene with alkyl diazoacetate. However, the product in this reaction is a mixture of alkyl cis-chrysanthemate and alkyl trans-chrysanthemate. For this reason, the conversion of the cis-isomer thus produced into the corresponding transisomer is necessary in order to increase the insecticidal efficiency.

As the method for achieving such conversion, there is known the treatment of the cis-isomer with a not less than equal molar amount of alkali metal tertiary alkoxide in benzene while heating [French patent No. 1,203,902]. This treatment is, however, not advantageous when using a relatively large amount of expensive alkali metal tertiary alkoxide. There is also known the treatment of the cis-isomer with a catalytic amount of alkali metal alkoxide in a lower primary alcohol at 150° to 200°C [Japanese provisional patent No. 6457/65]. This treatment is disadvantageous in requiring an autoclave for maintaining a high pressure in the reaction.

As the result of an extensive study, it has been found that treatment of alkyl cis-chrysanthemate with a catalytic amount of alkali metal alkoxide in the absence of any solvent makes it possible to isomerize the cis-isomer into the corresponding trans-isomer with ease even at a low temperature around 50°C and under an atmospheric pressure. This finding is of unexpected and surprising nature, because the isomerization by the use of an alkali metal alkoxide wherein the alkoxy moiety is derived from a lower primary alcohol (e.g. methanol, ethanol) has been understood to be successfully achieved only under specific conditions as described in Japanese provisional patent No. 6457/65.

According to the present invention, there is provided a process for preparing alkyl trans-chrysanthemate which comprises treating the corresponding cis-isomer with a catalytic amount of alkali metal alkoxide at a temperature of about 50° to 200°C.

The alkyl cis-chrysanthemate to be used in this invention is representable by the formula:

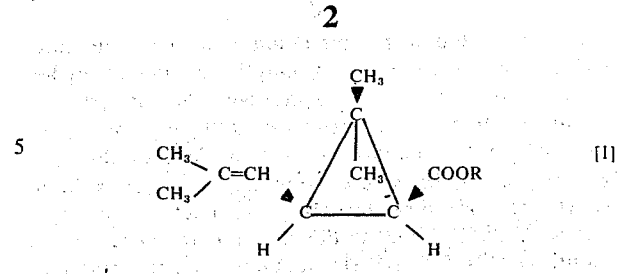

wherein R is a lower alkyl group. The term "lower alkyl" hereinabove used is usually intended to mean the one having 1 to 8 carbon atoms and includes specifically methyl, ethyl, n-propyl, isopropyl, n-butyl, isobutyl, t-butyl, etc. Since the increase in the number of carbon atoms of the lower alkyl group generally results in the decrease of the isomerization efficiency, the methyl and ethyl esters are particularly preferred.

The starting cis-isomer [I] may be used alone or in a mixture with the corresponding trans-isomer, i.e. alkyl trans-chrysanthemate, which is representable by the formula:

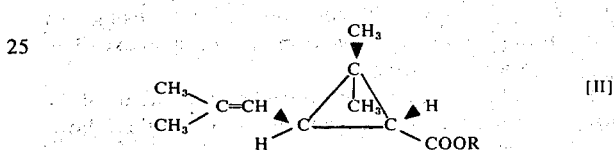

wherein R is as defined above.

The alkali metal alkoxide to be employed as the catalyst may be an alkali metal lower alkoxide (e.g. sodium methoxide, sodium ethoxide, potassium methoxide, potassium ethoxide, lithium ethoxide), and the alkoxy moiety may be the one derived not only from a primary alcohol but also from a secondary or tertiary alcohol. From the economical viewpoint, the use of the one the alkoxy moiety is derived from a lower primary alcohol, particularly of sodium methoxide or sodium ethoxide, is favored.

Concerning the amount of the catalyst, i.e. alkali metal alkoxide, with respect to the starting cis-isomer [I] or its mixture with the corresponding trans-isomer [II], no strict limitation is present, and it may be appropriately decided depending on the reaction time, the type of catalyst and the like. Usually, the catalyst may be used in a proportion of 1/100 to 1/5 mol per 1 mol of the starting ester.

The process of this invention may be carried out batchwise or continuously. The reaction can proceed without any correlation to the pressure. When effected under an atmospheric pressure, the starting ester may be introduced into the reaction together with the catalyst. If desired, the starting ester may be added into the reactor continuously or intermittently depending on the progress of the reaction. The reaction temperature is usually from about 50° to 200°C, preferably from 70° to 180°C. In case of the reaction temperature being lower than 50°C, the reaction rate of isomerization becomes too slow. In case of the reaction temperature being considerably higher than 200°C, unfavorable phenomena such as decomposition of the starting ester will be observed. The reaction proceeds without using any solvent but, if desired, an aprotic solvent may be employed.

In order to accomplish the isomerization more safely and efficiently, the adoption of an inert gas atmosphere is recommended. It is also recommendable to eliminate sufficiently the water which may be contained in the starting ester prior to its contact with the catalyst.

The reaction time is associated with the amount of the catalyst, the reaction temperature and the like. In general, a higher reaction temperature results in a shorter reaction time. Insofar as the reaction is carried out within the range of the reaction temperature as mentioned above, no strict regulation on the reaction time is necessary.

The proceeding of the reaction may be checked by a per se conventional procedure such as gas chromatography, IR absorption spectrum or the like.

After the isomerization is completed, the reaction mixture may be subjected to distillation to give the alkyl transchrysanthemate of the formula [II]. Alternatively, the reaction mixture may be subjected to hydrolysis whereby transchrysanthemic acid is obtained.

As understood from the above descriptions, the process of this invention is industrially advantageous, because the isomerization can proceed easily in the presence of a catalytic amount of alkali metal alkoxide under a relatively mild condition without using any solvent to give the objective transisomer in an excellent yield and a high purity.

Practical and presently preferred embodiments of the present invention are illustratively shown in the following Examples.

EXAMPLE 1

In a 100 ml volume flask equipped with a condenser, there was charged ethyl cis-chrysanthemate (25.0 g). Under the nitrogen atmosphere, sodium ethoxide (1.0 g) was added thereto, and the resultant mixture was heated at 130°C while stirring. The results of the gas chromatographic analysis of the reaction mixture sampled 10, 30, 60, 120 and 180 minutes after the initiation of the reaction are shown in the following Table:

| Reaction time (minutes) | cis-Isomer (% by weight) | trans-Isomer (% by weight) |
|---|---|---|
| 10 | 84.4 | 15.6 |
| 30 | 59.9 | 40.1 |
| 60 | 32.7 | 67.3 |
| 120 | 10.3 | 89.7 |
| 180 | 8.8 | 91.2 |

After the isomerization, the reaction mixture was distilled under reduced pressure to give ethyl trans-chrysanthemate (22.0 g). B.P. 88°C/5 mmHg. Hydrolysis of this product in a conventional manner afforded trans-chrysanthemic acid. M.P. 49° to 54°C.

EXAMPLE 2

The reaction was effected as in Example 1 but changing the reaction temperature. The results are shown in the following Table:

| Reaction temperature (°C) | trans-Isomer (% by weight) | | | |
|---|---|---|---|---|
| | 30 minutes | 60 minutes | 120 minutes | 180 minutes |
| 70 | 16.1 | 30.4 | 52.6 | 69.9 |
| 100 | 30.0 | 48.5 | 73.3 | 86.2 |
| 150 | 45.7 | 75.8 | 88.4 | 90.4 |
| 170 | 56.4 | 86.2 | 88.5 | 89.4 |

EXAMPLE 3

In a 300 ml volume flask, a mixture of ethyl cischrysanthemate and ethyl trans-chrysamthemate (35.2 : 64.8 by weight) (100 g) was charged and, under the nitrogen atmosphere, sodium ethoxide (4.0 g) was added thereto. The resulting mixture was heated on an oil bath at 130°C while stirring. The results of the gas chromatographic analysis of the reaction mixture sampled 60, 120 and 180 minutes after the initiation of the reaction are shown in the following Table:

| Reaction time (minutes) | cis-Isomer (% by weight) | trans-Isomer (% by weight) |
|---|---|---|
| 60 | 10.7 | 89.3 |
| 120 | 9.2 | 90.3 |
| 180 | 8.8 | 91.2 |

The reaction mixture was hydrolyzed with a 25 % aqueous solution of sodium hydroxide and acidified with sulfuric acid to give trans-chrysanthemic acid (80.3 g). M.P. 48° to 53°C.

EXAMPLE 4

The reaction was effected as in Example 3 but changing the reaction temperature. The results are shown in the following Table wherein the yield is calculated by the following equation:

$$\text{Yield (\%)} = \frac{\text{Amount of mixture of cis-isomer and trans-isomer recovered (g)}}{\text{Amount of feed (g)}} \times 100$$

| Reaction temperature (°C) | trans-Isomer (% by weight) | | | | Yield (%) |
|---|---|---|---|---|---|
| | 30 minutes | 60 minutes | 120 minutes | 180 minutes | |
| 100 | 84.5 | 88.6 | 90.3 | 92.3 | 97.0 |
| 120 | 88.4 | 90.1 | 91.8 | — | 96.9 |
| 140 | 90.2 | 90.6 | 91.1 | — | 96.9 |
| 150 | 90.3 | 91.0 | — | — | 96.6 |
| 170 | 89.7 | 89.6 | — | — | 96.5 |

EXAMPLE 5

The reaction was effected as in Example 3 but changing the amount of sodium ethoxide. The results are shown in the following Table:

| Amount of sodium ethoxide (g) | Reaction temperature (°C) | Reaction time (minutes) | trans-Isomer (% by weight) | Yield (%) |
|---|---|---|---|---|
| 3.0 | 130 | 240 | 90.1 | 96.8 |
| 5.0 | 130 | 120 | 91.3 | 95.0 |
| 6.0 | 130 | 60 | 91.4 | 94.1 |

EXAMPLE 6

As in Example 1, a mixture of ethyl cis-chrysanthemate and ethyl trans-chrysanthemate (35.2 : 64.8 by weight) (25.0 g) was treated with sodium methoxide (1.0 g) at 130°C for 120 minutes while stirring. After cooling, the reaction mixture was hydrolyzed with a 25 % aqueous solution of sodium hydroxide and acidified with sulfuric acid. By IR absorption spectrum and gas chromatographic analysis, the obtained acidic product was confirmed to be a mixture of cis-chrysanthemic acid and trans-chrysanthemic acid in a weight ratio of 10 : 90.

EXAMPLE 7

As in Example 1, n-propyl cis-chrysanthemate (25.0 g) was treated with sodium ethoxide (1.0 g) at 140°C for 120 minutes while stirring. After cooling, the reaction mixture was subjected to hydrolysis by a conventional procedure. By IR absorption spectrum and gas chromatographic analysis, the obtained acidic product was confirmed to be a mixture of cis-chrysanthemic acid and trans-chrysanthemic acid in a weight ratio of 20 : 80.

EXAMPLE 8

As in Example 1, n-butyl cis-chryanthemate (25.0 g) was treated with sodium ethoxide (2.0 g) at 150°C for 60 minutes while stirring. By gas chromatographic analysis, the product was confirmed to be a mixture of the cis-isomer and the trans-isomer in a weight ratio of 25 : 75. The product was hydrolyzed by a conventional procedure and cis-chrysanthemic acid was removed as dihydro-chrysanthemolactone to give trans-chrysanthemic acid (15.1 g).

What is claimed is:

1. A process for preparing an alkyl trans-chrysanthemate which comprises treating the corresponding cis-isomer with an alkali metal lower alkoxide in the amount of about 1/100 to 1/5 mole of said alkali metal lower alkoxide per 1 mole of the starting cis-isomer at a temperature of about 50° to 200°C. in the absence of a solvent.

2. The process according to claim 1, wherein the alkali metal lower alkoxide is sodium methoxide or sodium ethoxide.

3. The process according to claim 1, followed by the hydrolysis of the resulting alkyl trans-chrysanthemate to the corresponding free acid.

4. The process according to claim 1, wherein the alkali metal lower alkoxide is derived from a primary alcohol.

5. The process according to claim 1, wherein the alkali metal lower alkoxide is sodium methoxide, sodium ethoxide, potassium methoxide, potassium ethoxide or lithium ethoxide.

6. The process according to claim 1, wherein the reaction temperature is from about 70°C. to 180°C.

* * * * *